United States Patent [19]

Borchard

[11] Patent Number: 4,962,868

[45] Date of Patent: Oct. 16, 1990

[54] APPARATUS FOR DISPENSING A CONTROLLED DOSE OF A LIQUID FLUID

[75] Inventor: Hans-Jürgen Borchard, Berlin, Fed. Rep. of Germany

[73] Assignee: Henning Berlin GmbH, Berlin, Fed. Rep. of Germany

[21] Appl. No.: 326,389

[22] Filed: Mar. 21, 1989

[30] Foreign Application Priority Data

Mar. 25, 1988 [DE] Fed. Rep. of Germany ....... 3810262

[51] Int. Cl.$^5$ .............................................. B67D 5/22
[52] U.S. Cl. ...................................... 222/49; 222/182; 222/386; 222/309; 604/210; 604/234; 128/200.14
[58] Field of Search ........................ 604/220, 229, 234; 222/44, 47, 49, 50, 182, 309; 664/386, 208, 210, 207; 128/200.14; 239/320, 275

[56] References Cited

U.S. PATENT DOCUMENTS

| 963,051 | 7/1910 | Kooken | 604/208 |
| 1,269,922 | 6/1918 | Gadecki | 222/386 |
| 1,742,157 | 12/1929 | Christian | 222/386 |
| 2,250,758 | 7/1941 | French | 222/386 |
| 2,434,875 | 1/1948 | Turnbull et al. | 604/207 |
| 2,648,334 | 8/1953 | Brown et al. | 604/208 |
| 4,112,945 | 9/1978 | Helixon et al. | 604/220 |
| 4,127,126 | 11/1978 | Schunk . | |
| 4,475,905 | 10/1984 | Himmelstrup | 604/208 |

FOREIGN PATENT DOCUMENTS 8509572 8/1985 Fed. Rep. of Germany .

Primary Examiner—H. Grant Skaggs
Attorney, Agent, or Firm—Henry M. Feiereisen

[57] ABSTRACT

An apparatus for dispensing a controlled dose of a liquid fluid such as a liquid medication includes a dispenser head which is snugly fitted over the needle-shaped end of a syringe filled with the liquid pharmaceutical and including a piston in fully retracted or drawn position. The syringe with its fully drawn piston is completely encased and protected by a tube which is connected to the dispenser head.

15 Claims, 2 Drawing Sheets

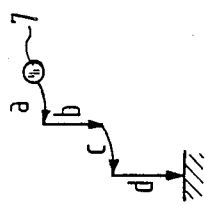
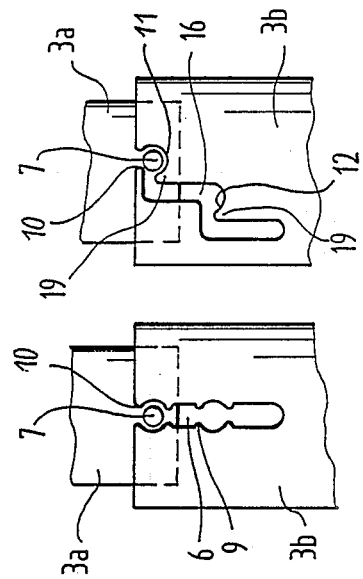
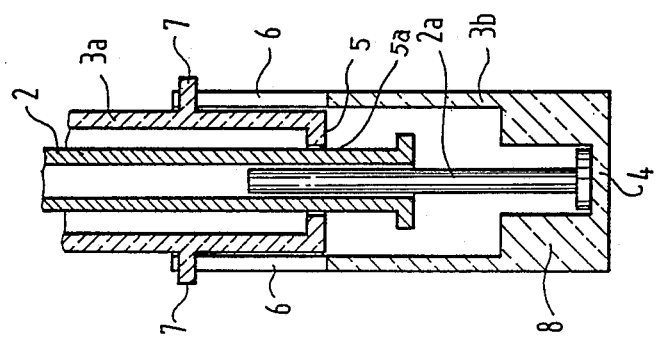

APPARATUS FOR DISPENSING A CONTROLLED DOSE OF A LIQUID FLUID

BACKGROUND OF THE INVENTION

The present invention refers to an apparatus for dispensing a controlled dose of a liquid fluid, such as a liquid pharmaceutical, and in particular to a dispensing apparatus for nasal administering of such a pharmaceutical.

Pharmaceutical agents are commonly administered in substances which contain a unit dose of the respective agents. Those agents which should be injected are usually commercialized in form of ampoules which contain the dose to be administered. For hygienic reasons, such form of dosages is desirable because a repeated withdrawal from a larger supply of pharmaceutical and subsequent metering in single doses is avoided. On the other hand, when liquid pharmaceuticals are concerned which are directly administered to the patient, the commercialization of such single doses is troublesome because they usually require a simultaneous supply of expensive dispensing devices which render the distribution of numerous pharmaceuticals in single doses practically impossible.

This is especially true for the nasal application of liquid pharmaceuticals which are administered by evenly spraying a pharmaceutical via a spray head in each nostril of the nose. Spray devices are relative expensive and thus are designed for multiple application which is, however, undesired when administering pharmaceuticals which for diagnostic purposes should be delivered into the nostrils only once. Although it would be possible to exchange the spray heads or to use respective tops; in case a medication is concerned which is rarely used in a professional office, there is still the drawback that a physician has to store a large supply of such a medication even when only sparingly using it. Such a case is conceivable for example, for diagnostics of thyroid diseases during administering of thyrotropin-releasing-hormone as single dose to a patient for determining thyroid conditions based on the increase of the serum level of thyrotropin.

For various reasons such as compatibility, the nasal application of a test dose is especially desirable. Since, however, the test dose should be administered only once and evenly in both nostrils, the spraying devices used for such purposes proved to be too complicated and too expensive so that the price of such medications or pharmaceuticals increased significantly.

SUMMARY OF THE INVENTION

It is thus an object of the present invention to provide an improved apparatus for dispensing a controlled dose of a liquid pharmaceutical obviating the afore-stated drawbacks.

This object and others which will become apparent hereinafter are attained in accordance with the present invention by providing a dispenser head snugly fitted over the facing end of a syringe which is filled with liquid fluid and includes a piston in retracted or drawn position and by encasing the fluid-containing syringe and the drawn piston with a tube attached to the dispenser head.

The provision of such a dispensing apparatus allows the use of inexpensive and conventional material like syringes and atomizer heads which are combined so as to render the dispensing apparatus according to the invention inexpensive and yet reliable in operation.

The dosage to be administered is provided through the suitably filled syringe which is enclosed by the tube to allow safe transport and commercialization. Suitably, the bottom of the tube acts a stop for the piston which thus bears with its respective end against the bottom so as to be prevented from being dissociated from the syringe.

According to a further feature of the present invention the tube is composed of two telescopic tubular members which are linked by a suitable pin-groove arrangement to thereby allow the delivery of two controlled doses but also to protect against accidental actuation i.e. axial displacement of the tubular members and thus pushing of the piston into the syringe. Suitably, one tubular member may include a groove which is sectionized by constrictions into straight sections, with the length of each straight section corresponding to one controlled dose of predetermined quantity. The constrictions are elastic so that a certain resistance is applied against actuation of the tubular members which resistance can, however, be overcome when desiring to administer the controlled doses.

BRIEF DESCRIPTION OF THE DRAWING

The above and other objects, features and advantages of the present invention will now be described in more detail with reference to the accompanying drawing in which:

FIG. 2 is a partial longitudinal section of the dispensing apparatus of FIG. 1;

FIG. 3a is a partial schematic view of the dispensing apparatus of FIG. 1 illustrating in detail elements for allowing a step-by-step administration of a pharmaceutical;

FIG. 3b is a partial schematic view of another embodiment of a dispensing apparatus according to the present invention illustrating in detail modified elements for allowing a step-by-step administration of a pharmaceutical; and FIG. 3c is a schematic illustration of the sequence of actuations required to operate the dispensing apparatus as partially shown in FIG. 3b.

DETAILED DESCRIPTION OF PREFERRED EMBODIMENTS

Figure 1:
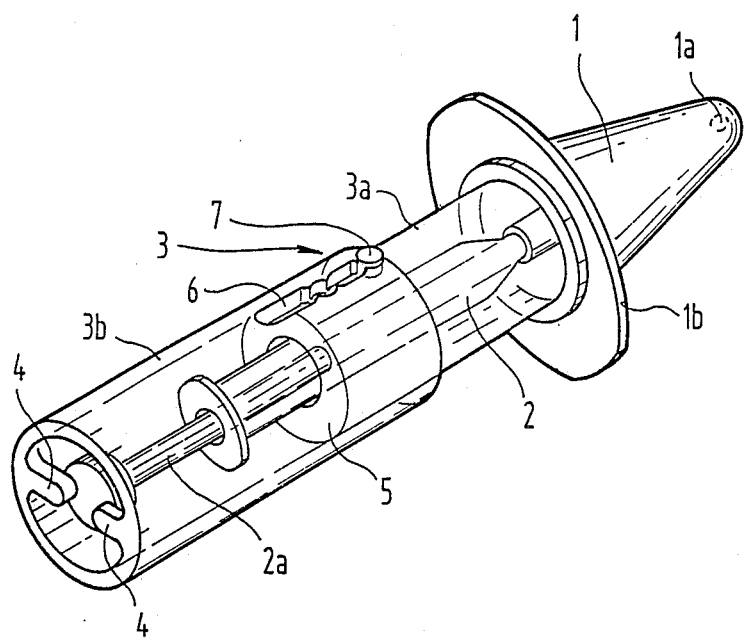
FIG. 1 is a schematic perspective illustration of one embodiment of a dispensing apparatus in accordance with the present invention.

Referring now to the drawing, and in particular to FIG. 1, there is shown a schematic perspective view of one embodiment of a dispensing apparatus for delivering controlled doses of a liquid pharmaceutical or medication. The dispensing apparatus includes a dispenser head 1 such as a spray head with a spray nozzle 1a for forming a mist of small drops of the liquid pharmaceutical The spray head is a conventional part which is usually combined with a pump and may be a simple injection molded part of plastic material with a narrow central channel for the fluid. For facilitating actuation of the dispensing apparatus, the dispenser head 1 is provided with a collar 1b to allow the dispenser head 1 to be easily held between two fingers.

The dispenser head 1 is fitted snugly onto the front needle section of a syringe 2 which is commonly made of a glass tube or plastic tube and accommodates a piston 2a slidably guided in the syringe 2 to draw and inject the liquid pharmaceutical. Since the syringe 2 is tightly connected to the dispenser head 1, the pressure, which is generated during pushing of the piston 2a into the syringe 2, is transmitted without loss to the spray nozzle 1a.

Although a dispensing apparatus comprising the dispensing head 1 and the syringe 2 allows atomizing of the liquid pharmaceutical contained in the syringe 2, it still does not ensure a reliable delivery of a controlled dose and, moreover, can break or crack too easily for use as a commercial product. Therefore, in order to be protected against bending or unintentional axial actuation, the syringe 2 containing the liquid pharmaceutical and the piston 2a which is in the drawn or retracted position are completely surrounded by a tube, preferably made of opaque and/or transparent plastic material and generally designated by reference numeral 3.

Turning now to FIG. 2 which shows a partial longitudinal section of the dispensing apparatus, it can be seen that the tube 3 includes two tubular members 3a, 3b which are telescopically connected to each other, with the tubular member 3a being stationary and nesting into the tubular member 3b. The forward end of the tubular member 3a is suitably connected to the dispenser head 1 (FIG. 1) while the rear section of the tube member 3a slides within the tubular member 3b. The outer diameter of the tubular member 3a corresponds essentially to the inside diameter of the tubular member 3b so that the latter can slide along the outside surface of the tubular member 3a. At its distant end to the dispenser head 1, the tubular member 3b has a bottom 4 which ensures that during an axial movement of the tubular member 3b, the piston 2a is pushed in axial direction simultaneously therewith so that the liquid pharmaceutical contained in the syringe 2 can be administered to a patient. The rearward end of the tubular member 3b may be completely closed by the bottom 4 as shown in FIG. 2, or, alternatively, the bottom 4 may also be designed as shown in FIG. 1 i.e. with inwardly directed stops against which the piston 2a abuts.

In order to ensure a simple assembly and to avoid a tilting of the syringe 2 during actuation, the syringe 2 and the piston 2a are suitably guided in coaxial arrangement by suitable guides defined by the tubular members 3a, 3b. Accordingly, as shown in FIG. 2, the tubular member 3a is provided at its distant end to the dispenser head 1 with a bottom 5 which includes a central through-opening 5a for guiding the syringe 2 at suitable clearance. For ensuring a coaxial movement during its forward push, the free end of the piston 2a is fittingly received in a pocket hole 8 of the tubular member 3b.

The tubular member 3a is further provided at opposite locations thereof with a pin or projection 7 which cooperates with an associated groove 6 in the tubular member 3b. The groove 6 defines a guideway for the pin 7 as shown in particular in FIG. 3a and is divided in predetermined sections by elastic constrictions 9 so that controlled doses of the content in the syringe 2 can be administered. In addition, the cooperation of the pin 7 with the groove 6 protects the piston 2a against accidental pushing and thus axial movement when being in the fully drawn position in which the syringe 2 is charged with fluid because the pin 7 and hence the tubular member 3b are prevented from axial movement by the respective constriction 9. Only when deliberately applying a certain force can the tubular member 3b be pushed relative to the tubular member 3b and thus the pin 7 past the elastic constriction 9.

The distance between successive constrictions 9 corresponds to one exact dose of fluid to be administered. Thus, when pushing inwardly the tubular member 3b by a force sufficient to overcome the constriction 9, a controlled dose of pharmaceutical is delivered through the spray nozzle 1a until the pin 7 is again caught between the constrictions 9 which resist a further axial movement of the piston 2a into the syringe 2.

An accidental pulling out or dissociation of the tubular member 3b from the tubular member 3a is prevented by a constriction 10 at the forward end of the groove 6.

Turning now to FIG. 3b, there is shown a modified groove 16 which ensures in cooperation with the pin 7 that even when unintentionally applying a force upon the tubular member 3b which force would be sufficient to overcome the constrictions 9 as shown in FIG. 3a, the tubular member 3b and thus the piston 2a will not be axially moved to deliver a dose. The groove 16 according to FIG. 3b is provided in the shape of a step-shaped curved track by which two controlled doses can be administered. In order to deliver each dose, the course of the groove 16 requires two successive motions in order to actuate the piston 2a appropriately.

In the retracted or drawn position of the piston 2a, the pin 7 is received in an enlargement or pocket 11 of the groove 16. Constriction 10 prevents an accidental axial detachment of the tubular member 3b from tubular member 3a. To deliver a first dose of pharmaceutical, the tubular member 3b is turned relative to the tubular member 3a to align the pin 7 with a first straight section of the groove 16. Preferably, a further constriction 19 defined by an elastic nose of the tubular member 3b is provided at the exit of pocket 11 for creating a certain resistance against turning of tubular member 3b so as to safeguard against unintentional actuation. After aligning the pin 7 with the straight section of the groove 16, the tubular member 3b and thus the piston 2a can be axially pushed forward until the pin 7 is received in a second pocket 12. The length of the straight section of the groove 16 corresponds to one controlled dose.

After delivering a first dose, the pin 7 is securely retained in the pocket 12 and prevented from further axial pushing of the tubular member 3b unless the tubular member 3b is again turned relative to the tubular member 3a until the pin 7 is aligned with a second straight section of the groove 16 at which point a second controlled dose can be delivered. The exit of the pocket 12 again includes an elastic constriction 19 to create some resistance against the turning action. The sequence of turning motions and advance motions to deliver two doses of liquid pharmaceutical is schematically illustrated in FIG. 3c by arrows a, b, c, d.

The content of the syringe 2 is delivered in two controlled doses, with the quantity of each dose being predetermined by the length of the respective straight section of groove 16. Evidently, the dispensing apparatus can be used to deliver three or more such controlled doses by suitably modifying the groove 16 to include an equivalent number of straight sections.

It will be appreciated that an accidental axial pushing of the tubular members relative to each other may also be prevented by removable safety elements such as e.g. an adhesive tape. Also variations of the groove-and-pin arrangement for obtaining a delivery of controlled doses other than those shown should be considered within the scope of the invention. For example, it is possible to provide spring-biased or elastic pins which cooperate with suitable grooves and are required to be pressed in order to allow an advance of the movable tubular member.

Although, FIGS. 1 and 2 show the tubular member 3a to be of smaller diameter than the tubular member 3b, it is certainly possible to modify the dispensing apparatus by providing the other tubular member i.e. tubular member 3b with the smaller diameter which then would slide within the tubular member 3a. Certainly, the pin-and-groove arrangement may be provided vice versa, with the tubular member 3a including the groove and with the tubular member 3b provided with the pin. Also guides other than those shown in the drawing may be suitable to attain the same results.

It will be appreciated that the number of telescopic tubular members should not be considered as limited to two. Certainly, the use of more than two such telescopic tubular members is possible if such is desired. Moreover, the telescopic tubular members 3a, 3b may be substituted by a single tube for enclosing and protecting the syringe 2 with the drawn piston 2a. In this case, the tube is removably attached to the dispenser head 1 so that before using the apparatus, the tube is removed to allow access to the syringe 2. Stops which may be suitably arranged on the syringe 2 or on the drawn part of the piston 2a can then attain the step-by-step pushing of the piston 2a.

Although the dispensing apparatus according to the invention has been described in connection with the nasal application of a controlled dose of a certain pharmaceutical preparation, it should be noted that certainly other applications are feasible as well. Evidently, the dispensing apparatus according to the invention may be usable for distribution of charged syringes for all kinds of purposes, with the dispenser head suitably substituted by a simple protective cap. Further, the dispensing apparatus may be usable for dropwise administering of pharmaceuticals such as antibiotics-containing eyedrops by appropriately modifying the dispenser outlet. Finally, the dispensing apparatus is not only limited to spraying the liquid pharmaceutical into the nostrils but could be employed for all body openings such as for example the throat.

While the invention has been illustrated and described as embodied in an apparatus for dispensing a controlled dose of a liquid fluid, it is not intended to be limited to the details shown since various modifications and structural changes may be made without departing in any way from the spirit of the present invention.

What is claimed as new and desired to be protected by Letters Patent is set forth in the appended claims:

I claim:

1. Apparatus for nasal administration of a controlled dose of a liquid medication through atomizing the liquid medication, comprising:
    a spray head provided with a spray nozzle through which the liquid medication is delivered;
    fluid-containing means including a syringe which is filled with liquid medication and has a forward portion snugly connected to said spray head and a piston slidably guided in said syringe for delivering the medication;
    encasing means connected to said spray head and completely surrounding said fluid-containing means, with said piston being initially in retracted position, said encasing means including at least two telescopic tubular members slidable relative to each other between an extended position and a fully depressed position for actuating said piston; and
    control means for stepwise actuation of said piston to allow delivery of a controlled dose of liquid medication into each nostril, said control means including at least one groove-pin arrangement by which said tubular members are lockable relative to each other in the extended position and in at least one intermediate position before reaching the fully depressed position.

2. Apparatus as defined in claim 1 wherein said forward portion of said syringe is shaped in form of a needle.

3. Apparatus as defined in claim 1 wherein one of said tubular members is fixedly connected to said spray head and said other tubular member defines a stop acting against said piston at the facing end thereof for pushing said piston in an axial direction when sliding said other tubular member relative to said one tubular member.

4. Apparatus as defined in claim 3, and further comprising guide means connected to said tubular members for ensuring a coaxial alignment of said fluid-containing means within said encasing means.

5. Apparatus as defined in claim 4 wherein said guide means is a bottom of said one tubular member, said bottom being provided with a central through-opening by which said fluid-containing means is guided.

6. Apparatus as defined in claim 4 wherein said guide means is a bottom of said other tubular member, said bottom defining said stop and including a pocket hole for receiving said facing end of said fluid-containing means.

7. Apparatus as defined in claim 1 wherein said groove-pin arrangement includes at least one groove mounted to one of said tubular members and at least one pin mounted to said other one of said tubular members and projecting into said groove, said groove being provided with spaced elastic constrictions for retaining said pin at said initial position and said intermediate position of said tubular members.

8. Apparatus as defined in claim 7 wherein said groove is of elongated shape in direction of said axis of said tubular members.

9. Apparatus as defined in claim 7 wherein said groove describes a stepped curved path, with each step defining a quantity of a dose.

10. Apparatus as defined in claim 9 wherein said groove includes at least first and second straight sections offset to each other and extending in direction of said axis of said tubular members, each of said straight sections of said groove being defined by a length corresponding to the delivery of one controlled dose.

11. Apparatus as defined in claim 10 wherein said first straight section has one end connected to one end of said second straight section by a transversely extending section, and wherein said groove includes a further transversely extending section connected to the other end of said first straight section so that an axial displacement between said tubular members requires a preceding turning motion of said tubular members relative to each other.

12. Apparatus as defined in claim 11 wherein each of said radially extending sections has an elastic constriction at its junction to said straight sections, said constrictions providing a surmountable resistance to the turning motion.

13. Apparatus as defined in claim 1 wherein said tube is made of opaque plastic material.

14. Apparatus as defined in claim 1 wherein said tube is made of transparent plastic material.

15. Apparatus as defined in claim 1 wherein said encasing means is made of opaque plastic material and transparent plastic material.

* * * * *